United States Patent [19]

Adam

[11] 4,407,659

[45] Oct. 4, 1983

[54] DRIVE SYSTEM

[75] Inventor: Leslie E. S. Adam, Doncaster, Australia

[73] Assignee: Varian Associates, Inc., Palo Alto, Calif.

[21] Appl. No.: 346,073

[22] PCT Filed: Jun. 5, 1981

[86] PCT No.: PCT/AU81/00069

§ 371 Date: Jan. 28, 1982

§ 102(e) Date: Jan. 28, 1982

[87] PCT Pub. No.: WO81/03545

PCT Pub. Date: Dec. 10, 1981

[30] Foreign Application Priority Data

Jun. 6, 1980 [AU] Australia ............................ PE3939

[51] Int. Cl.3 ............................................ A61M 5/20

[52] U.S. Cl. ............................................ 604/155

[58] Field of Search ............ 128/218 A, DIG. 1, 224, 128/234, 236; 604/154, 155, 131

[56] References Cited

U.S. PATENT DOCUMENTS

| | | | |
|---|---|---|---|
| 2,627,270 | 2/1953 | Glass | 128/DIG. 1 |
| 3,313,291 | 4/1967 | Marshall | 128/218 A X |
| 3,701,345 | 10/1972 | Heilman et al. | 128/218 A X |
| 3,701,350 | 10/1972 | Guenther | 128/DIG. 1 |
| 4,191,187 | 3/1980 | Wright | 128/218 A |
| 4,255,096 | 3/1981 | Coker, Jr. et al. | 128/218 A X |

*Primary Examiner*—John D. Yasko

*Attorney, Agent, or Firm*—Stanley Z. Cole; Gerald M. Fisher; Edward H. Berkowitz

[57] ABSTRACT

A syringe drive system having a structure for supporting the body of a syringe in a particular disposition and retaining the syringe body against axial movement. A drive motor is secured to the structure so as to have a drive shaft thereof in alignment with the syringe body. The drive shaft is arranged to move axially in response to energization of the motor and is connected to the plunger stem of the syringe through a coupling which is slideably mounted on the support structure. The arrangement is such that energization of the motor causes movement of the coupling block in the axial direction of the syringe and the syringe plunger is depressed or withdrawn accordingly.

6 Claims, 4 Drawing Figures

DRIVE SYSTEM

This invention relates to controllable drive systems and is particularly concerned with such a drive system as applied to syringes as used to deposit samples for chemical analysis. One example application of the invention is in the field of spectroscopic analysis.

Syringe drive systems as used prior to the present invention have involved a motor connected to the syringe through the intermediary of a transmission mechanism such as a rack and pinion mechanism or a cam mechanism. Drive systems of that kind however, cannot provide a consistently accurate response because of backlash and other inherant characteristics, and consequently are not suited for some applications. For example, they are not satisfactory if a sample is to be deposited in sub-microliter volume with repeatable performance.

It is a principal object of the present invention to provide a syringe drive system which is relatively simple and is consistently accurate by comparison with prior systems.

A basic characteristic of the drive system of the present invention is that a motor is connected to the syringe through a single coupling as distinct from the relatively complicated mechanism of prior systems. Furthermore, the motor applies a drive force in the axial direction of the syringe and along a line substantially coincident with the syringe axis. The coupling merely serves as a means of ensuring syringe response to that force in either of two directions in which it may act.

In accordance with the present invention, there is provided a syringe drive system including, support means for receiving and holding the body of a syringe against axial movement, a drive motor connected to said support so as not to be movable relative thereto, a drive shaft connected to said motor and being movable axially in response to energization of said motor, the axis of said drive shaft being substantially parallel to the axis of said syringe body when held by said support means and coupling means connected to said drive shaft for movement therewith in said axial direction and being connectable to the plunger of said syringe so that said plunger moves axially of said syringe body in response to said axial movement of the drive shaft.

The essential features of the invention, and further optional features, are described in detail in the following passages of the specification which refer to the accompanying drawings. The drawings however are merely illustrative of how the invention might be put into effect, so that the specific form and arrangement of the features (whether they be essential or optional features) shown is not to be understood as limiting on the invention.

Figures 1, 2, 3, 4:
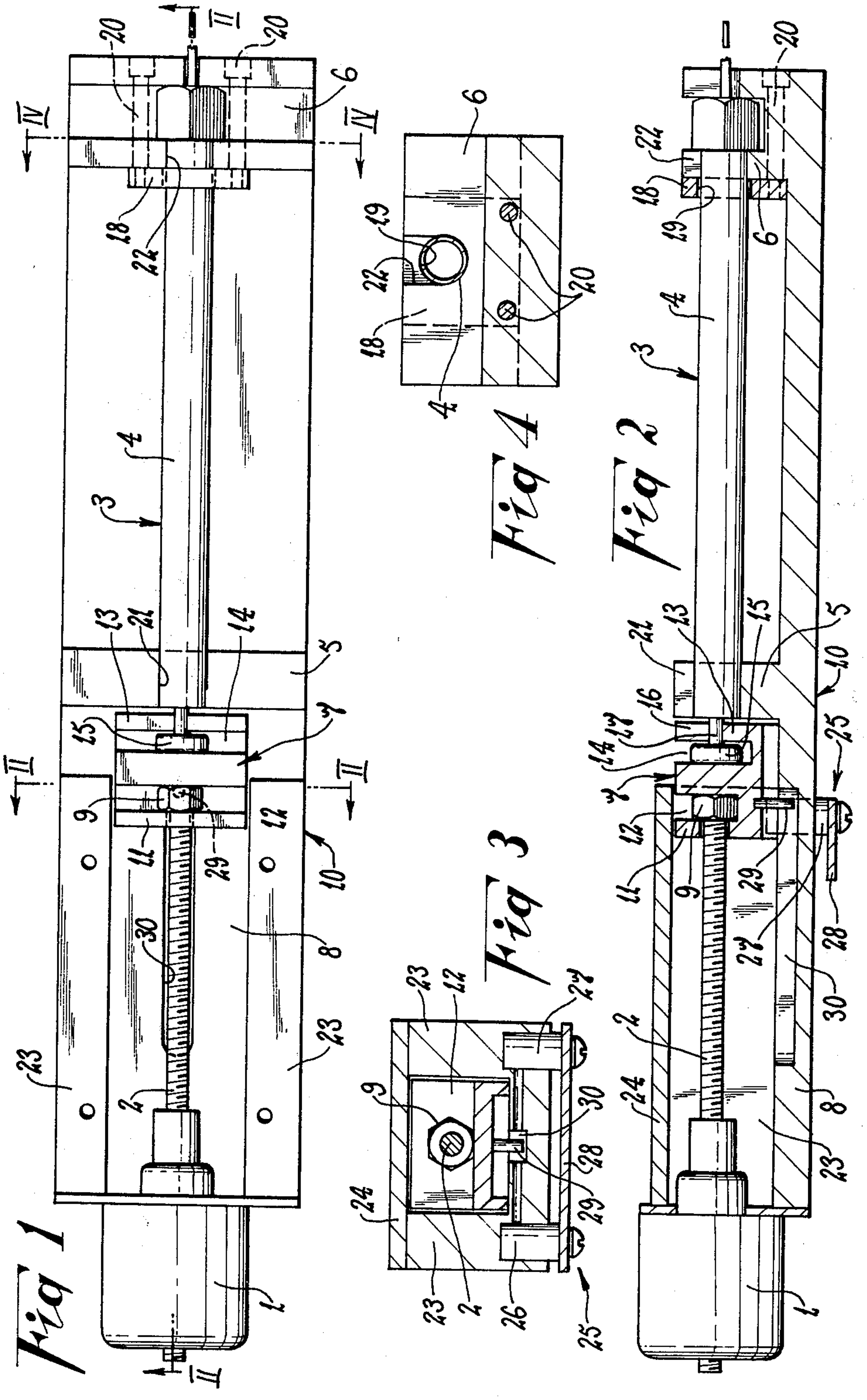
FIG. 1 is a plan view (with parts removed) of one embodiment of the invention.
FIG. 2 is a cross sectional view taken along line II—II of FIG. 1.
FIG. 3 is a cross sectional view taken along line III—III of FIG. 1.
FIG. 4 is a cross sectional view taken along line IV—IV of FIG. 1.

In a preferred embodiment of the invention as shown in the drawings, the drive motor 1 is a stepper or incremental advance motor having a drive shaft 2 which moves axially in response to energization of the motor 1. In the form shown, the motor 1 is electrically energized and has an internally threaded rotor (not shown) co-operating with an external thread of the drive shaft 2. Incremental advance or retraction of the shaft 2 is achieved by pulsed energization of the motor 1 and the rate and duration of such pulses may be varied according to circumstances. Accurate control of shaft movement can be achieved however, through appropriate electronics and the shaft 2 will remain fixed in position immediately upon termination of an energizing pulse.

A drive motor 1 as described is secured to a suitable support structure 10 for a syringe 3 so that the axis of the drive shaft 2 is substantially co-axial with the axis of the syringe body 4. In the arrangement shown, the support structure 10 includes two cradle supports 5 and 6 which engage respective opposite end portions of the syringe body 4 and any suitable clamping or other securing means may be employed to releaseably hold the syringe body 4 in the cradles 5 and 6. The cradles 5 and 6 are preferably arranged to automatically align the syringe body 4 with the motor drive shaft 2.

Connection of the syringe 3 and drive shaft 2 may be effected through a coupling block 7 which is slideably mounted on a base 8 of the support structure 10 and is attached to the outer end of the drive shaft 2 by a nut 9 or other appropriate means. In the preferred arrangement shown, the outer end of the drive shaft 2 extends through a rear portion 11 of the coupling block 7 and is secured against relative axial movement by the nut 9 which is located in a recess 12 of the block 7. A clamp screw or other means (not shown) may be provided in the block rear portion 11 to secure the shaft 2 against rotation relative to the block 7, but that can be attended to in a variety of other ways. The arrangement is such that energization of the motor 1 causes the coupling block 7 to move relative to the support structure 10 in the axial direction of the drive shaft 2.

The syringe 3 may be connected to the coupling block 7 in any appropriate manner. According to the embodiment shown, a front portion 13 of the coupling block 7 is provided with a recess 14 which receives the flange-like knob 15 of the syringe 3. A further and shallower recess 16 receives a part of the plunger stem 17 immediately adjacent the knob 15. The recess 14 confines the knob 15 against substantial axial movement relative to the coupling block 7 and, if desired, a resilient O-ring or other spacer means (not shown) may be provided between the knob 15 and one side of the recess 14 to prevent such axial movement. The plunger stem 17, or an axial boss (not shown) of the knob 15 may frictionally engage within the recess 16 and that recess 16 is preferably arranged to automatically align the plunger stem 17 with the motor drive shaft 2. That is, there is at least lateral alignment and in some cases vertical alignment might be also achieved when the stem 17 or boss engages the base of the recess 16.

In the construction shown, the syringe body 4 is held in place on the support structure 10 by a retainer plate 18. The plate 18 has a hole 19 therethrough which neatly receives the syringe body 4 and is releasably attached to the cradle support 6 by screws 20 or other fastening means. The cradle supports 5 and 6 have respective recesses 21 and 22 which neatly receive the syringe body 4 and locate it in substantial vertical alignment with the drive shaft 2.

It is generally preferred to form the coupling block 7 of "Delrin" or some other relatively low friction material. If desired, an appropriate guide may be provided on the support structure 10 to co-operate with the coupling block 7 and hold it to a straight path of travel. In the construction shown, that is achieved by confining the block 7 between two side walls 23 of the support structure 10. A cover 24 is removably attached to the walls 23 to provide a fully enclosed passage within which the block 7 can travel.

The discharge nozzle 25 of the syringe 3 projects for a suitable distance beyond the cradle support 6. The cradle support 5 may be omitted if desired since the adjacent end of the syringe 3 can be adequately supported by the coupling block 7 alone under some circumstances.

The fully withdrawn or ready to use position of the syringe plunger may be determined in any appropriate manner. In the construction shown, an optical switch 25 is used for that purpose. The switch includes a light source 26, receiver 27 and suitable circuitary 28 connected to a power supply. A pin 29 carried by the block 7 projects into a groove 30 provided in the base 8 and prevents light from the light source 26 impinging on the receiver 26 when the block 7 is at a position corresponding to the desired position of the syringe plunger. The switch 25 may function to prevent movement of the block 7 rearwardly beyond the aforementioned position.

A drive unit as described may be hand held or it may be fixed in location for automatic sequential sampling—e.g. for use as an accessory to a spectrophotometer. In the hand held mode, the unit may or may not incorporate integral electronics, according to requirements. The unit may be connected into a micro-processor so as to be fully programmable or it may be controlled through a step generator.

It has been found that a unit as described is capable of accurately dispensing volumes in the range of 0.25 ul to 100 ul inclusive, in increments of 0.25 ul. Repeatability has been measured at ±0.004 ul.

The unit is extremely simple as will be evident from the foregoing description and has the advantage of compactness and relatively light weight. Surprisingly that is achieved with an increase is accuracy as compared with prior syringe drive systems.

Finally, it is to be understood that various alterations, modifications and/or additions may be introduced into the constructions and arrangements of parts previously described without departing from the spirit or ambit of the invention as defined by the appended claims.

Having now described my invention, what I claim as new and desire to secure by Letters Patent is:

1. A syringe drive system including, a support structure, means on said support structure for receiving and holding a syringe against axial movement, a drive motor having a body and a drive shaft which moves axially relative to said body in response to energization of said motor, said drive motor body being secured to said support structure against movement relative thereto and so that said drive shaft is substantially coaxially with a said syringe secured to said support structure, coupling means connected directly to an end of said drive shaft for movement therewith relative to said support structure, said coupling means being directly connectable to the plunger of a said syringe to cause axial movement thereof in response to said axial movement of the drive shaft, and means holding said shaft against rotation relative to said support structure.

2. A syringe drive system according to claim 1, wherein said drive motor is a digital linear actuator which is energized by a pulsed signal.

3. A syringe drive system according to claim 1, wherein said support means includes a base, said coupling means includes a block slideably mounted on said base, said block being secured to said drive shaft for movement therewith in an axial direction of the shaft and having a recess therein for receiving an enlarged part of the syringe plunger which is located externally of the syringe body.

4. A syringe drive system according to claim 3, wherein said coupling block co-operates with guide means on said base so as to be held to a straight path of movement which is substantially parallel to the longitudinal axis of said plunger.

5. A syringe drive system according to claim 1, wherein an optical switch is connected to said support means and is operative to de-energize said drive motor when said plunger is withdrawn beyond a predetermined position.

6. A syringe drive system according to claim 5, wherein said optical switch includes a light source and a receiver located on respective opposite sides of said coupling block, and a member connected to said block is arranged to prevent light from said light source impinging on said receiver when said coupling block is at a position corresponding to said predetermined position of the plunger.

* * * * *